US012636501B2

(12) United States Patent
Young et al.

(10) Patent No.: US 12,636,501 B2
(45) Date of Patent: May 26, 2026

(54) IMPLANTABLE MEDICAL DEVICE CONFIGURED TO PROVIDE AN INTRACARDIAC FUNCTION

(71) Applicant: BIOTRONIK SE & Co. KG, Berlin (DE)

(72) Inventors: Daniel Young, Portland, OR (US); Christopher Jones, Oregon City, OR (US); Madeline Anne Midgett, Portland, OR (US); Brad McMillan, Lake Oswego, OR (US); Kurt Swenson, Dayton, OR (US); R. Hollis Whittington, Portland, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 262 days.

(21) Appl. No.: 18/558,439

(22) PCT Filed: Apr. 27, 2022

(86) PCT No.: PCT/EP2022/061232
§ 371 (c)(1),
(2) Date: Nov. 1, 2023

(87) PCT Pub. No.: WO2022/238123
PCT Pub. Date: Nov. 17, 2022

(65) Prior Publication Data
US 2024/0216696 A1 Jul. 4, 2024

Related U.S. Application Data

(60) Provisional application No. 63/187,454, filed on May 12, 2021.

(30) Foreign Application Priority Data

Jun. 15, 2021 (EP) .................................... 21179376

(51) Int. Cl.
*A61N 1/365* (2006.01)
*A61N 1/362* (2006.01)
*A61N 1/375* (2006.01)

(52) U.S. Cl.
CPC ............. *A61N 1/365* (2013.01); *A61N 1/362* (2013.01); *A61N 1/37512* (2017.08); *A61N 1/3756* (2013.01)

(58) Field of Classification Search
CPC .... A61N 1/365; A61N 1/362; A61N 1/37512; A61N 1/3756; A61N 1/3684; A61N 1/3682
See application file for complete search history.

(56) References Cited

U.S. PATENT DOCUMENTS

| | | | | |
|---|---|---|---|---|
| 2012/0165896 A1 | | 6/2012 | Stroebel | |
| 2013/0138006 A1* | | 5/2013 | Bornzin ................ | A61B 5/283 600/509 |

(Continued)

FOREIGN PATENT DOCUMENTS

| | | | |
|---|---|---|---|
| CN | 1942217 | A | 4/2007 |
| CN | 107427215 | A | 12/2017 |

(Continued)

OTHER PUBLICATIONS

European Search Report mailed on Nov. 26, 2021, by the European Patent Office for Application No. EP21179376.5 (5 pages).

(Continued)

*Primary Examiner* — Catherine M Voorhees
(74) *Attorney, Agent, or Firm* — Buchanan Ingersoll & Rooney PC

(57) ABSTRACT

An implantable medical device configured to provide for an intracardiac function comprises a body, a sensor arrangement arranged on the body and configured to receive a cardiac sense signal, and a processing circuitry operatively (Continued)

connected to the sensor arrangement. The processing circuitry is configured to process the cardiac sense signal received using the sensor arrangement to detect a signal deflection in the cardiac sense signal potentially indicative of an atrial event caused by atrial activity, and to start a peak detection window based on the detection of said signal deflection for determining a peak amplitude associated with said atrial event. The peak detection window comprises one or more sub-windows, the processing circuitry being configured to determine a candidate peak value in each sub-window and to set the peak amplitude based on the valid candidate peak values of the one or more consecutive sub-windows.

15 Claims, 6 Drawing Sheets

(56) References Cited

U.S. PATENT DOCUMENTS

2020/0094063 A1 3/2020 Hahn
2020/0179708 A1* 6/2020 Splett .................... A61B 5/076
2021/0023377 A1 1/2021 Muessig
2021/0085970 A1* 3/2021 Min ...................... A61N 1/365
2024/0075299 A1* 3/2024 Midgett ............... A61N 1/3756

FOREIGN PATENT DOCUMENTS

CN 109414582 A 3/2019
JP 200753373 A 11/2007
JP 2018510682 A 4/2018
JP 2019519326 A 7/2019
JP 2021020056 A 2/2021
WO 2006068145 A1 6/2006
WO 2008137536 A1 11/2008

OTHER PUBLICATIONS

International Search Report (PCT/ISA/210) and Written Opinion (PCT/ISA/237) mailed on Jul. 11, 2022, by the European Patent Office as the International Searching Authority for International Application No. PCT/EP2022/061232. (15 pages).

Office Action for Japanese Patent Application No. 2023-561190 dated Dec. 10, 2025 (with English Translation).

* cited by examiner

IMPLANTABLE MEDICAL DEVICE CONFIGURED TO PROVIDE AN INTRACARDIAC FUNCTION

CROSS-REFERENCE TO RELATED APPLICATIONS

This application is the United States National Phase under 35 U.S.C. § 371 of PCT International Patent Application No. PCT/EP2022/061232, filed on Apr. 27, 2022, which claims the benefit of European Patent Application No. 21179376.5, filed on Jun. 15, 2021, and U.S. Provisional Patent Application No. 63/187,454, filed on May 12, 2021, the disclosures of which are hereby incorporated by reference herein in their entireties.

TECHNICAL FIELD

The present invention generally relates to an implantable medical device for providing an intracardiac function, in particular a pacing function such as ventricular pacing, specifically VDD pacing.

BACKGROUND

In an implantable medical device, e.g., in the shape of a leadless pacemaker device or a cardiac stimulation device using a subcutaneously implanted pulse generator and one or multiple leads extending into a patient's heart, it may be desirous to provide stimulation in a ventricle of the patient's heart, e.g., in the right ventricle, in synchrony with atrial activity. For this, ventricular pacing shall take into account atrial sense signals to control the ventricular pacing based on atrial events indicative of atrial activity, for example in a so-called VDD pacing mode.

In recent years, leadless pacemakers have received increasing attention. Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

A leadless pacemaker or a lead of a stimulation device may specifically be designed for implantation in the right ventricle and, in this case, during implant is placed, e.g., in the vicinity of the apex of the right ventricle. Ventricular pacing may, for example, be indicated in case a dysfunction at the AV node occurs, but the sinus node function is intact and appropriate. In such a case in particular so-called VDD pacing may be desired, involving ventricular pacing with atrial tracking and hence requiring sensing of atrial activity in order to a pace in the ventricle based on intrinsic atrial contractions.

VDD pacing is in particular motivated by patient hemodynamic benefits of atrioventricular (AV) synchrony by utilizing an appropriate sinus node function to trigger ventricular pacing, potentially allowing to maximize ventricular preload, to limit AV valve regurgitation, to maintain low mean atrial pressure, and to regulate autonomic and neurohumoral reflexes.

Intracardiac Publications have explored solutions to use modalities to detect mechanical events of atrial contractions, including the sensing of motion, sound and pressure (see, for example, U.S. Publication No. 2018/0021581 disclosing a leadless cardiac pacemaker including a pressure sensor and/or an accelerometer to determine an atrial contraction timing). As mechanical events generally exhibit a small signal volume, signal detection based on mechanical events, for example motion, sound or pressure, may be difficult to sense, in particular when the implantable medical device is placed in the ventricle and hence rather far removed from the atrium of which contractions shall be sensed. In addition, wall motion and movement of blood generated by atrial contractions may not be directly translated to the ventricle, and cardiac hemodynamic signals, such as motion, heart sounds and pressure, are likely affected by external factors such as posture and patient activity.

The present disclosure is directed toward overcoming one or more of the above-mentioned problems, though not necessarily limited to embodiments that do.

SUMMARY

It is an objective to provide an implantable medical device and a method for operating an implantable medical device allowing, in particular, for ventricular pacing with atrioventricular synchrony, hence requiring reliable sensing of atrial events in order to provide for ventricular pacing based on such atrial events.

At least such desires are addressed by an implantable medical device configured to provide for an intracardiac function having the features of claim 1.

In one aspect, an implantable medical device configured to provide for an intracardiac function comprises a body, a sensor arrangement on the body and configured to receive a cardiac sense signal, and a processing circuitry operatively connected to the sensor arrangement. The processing circuitry is configured to process the cardiac sense signal received using the sensor arrangement to detect a signal deflection in the cardiac sense signal potentially indicative of an atrial event caused by atrial activity, and to start a peak detection window based on the detection of said signal deflection for determining a peak amplitude associated with said atrial event. The peak detection window comprises one or more sub-windows, the processing circuitry being configured to determine a candidate peak value in each sub-window and to set the peak amplitude based on the valid candidate peak values or the maximum of the valid candidate peak values of the one or more consecutive sub-windows.

Generally, in order to be able to provide for a cardiac function, such as a cardiac pacing function, it may be desired to sense atrial events, such that a pacing action may be provided with atrioventricular (AV) synchrony, for example in a VDD pacing mode. If the implantable medical device is implanted, e.g., in the ventricle, for example the right ventricle, cardiac sense signals relating to atrial activity however occur in the far-field and hence may have weak signal amplitudes and may be noisy.

When detecting an atrial event, a peak amplitude shall be determined which is associated with the atrial event. Based on the peak amplitude, for example a subsequent sense threshold is determined, the sense threshold being used in a subsequent cardiac cycle to detect an atrial event. By dynamically adapting the sense threshold based on an actual peak amplitude as measured for an atrial event, the reliability of sensing of atrial events over a sequence of cardiac cycles may be increased, hence limiting the number of missed cycles in which no atrial events are detected and increasing the likelihood that true atrial events are detected.

An atrial event, for example, is detected by comparing the cardiac sense signal to a sense threshold, wherein an atrial event is assumed to be present if a crossing of the sense threshold based on one or multiple signal values is identified.

If an atrial event is detected close to a subsequent ventricular event, signal portions relating to the atrial event may be corrupted by subsequent signal deflections relating to ventricular activity, wherein the ventricular signal deflections generally are much larger, as ventricular activity is detected in the near-field.

In another scenario, an atrial event may falsely be detected based on, for example, signal portions relating to a T wave in an intracardiac electrogram signal, T waves corresponding to ventricular repolarization and hence occurring in the near-field, such that also a T wave may exhibit a signal amplitude larger than signal deflections related to atrial activity. If portions of a T wave are falsely identified as an atrial event, the atrial event may be detected early, and with common approaches it may not be possible to obtain a reliable value for the peak amplitude associated with the true atrial event.

If based on a detection of an atrial event a peak amplitude is incorrectly determined, this may give rise to an incorrect update of the sense threshold and potentially an unreliable detection of atrial events in subsequent cycles.

For this reason, it herein is proposed to adopt a scheme for determining the peak amplitude in which a peak detection window is divided into multiple sub-windows, wherein in each sub-window a candidate peak value is determined and the actual peak amplitude is then set based on the candidate peak values as determined in the sub-windows. By dividing the peak detection window into different sub-windows, processing may be eased, as the different sub-windows may be processed separately to determine separate candidate peak values, and from the separate candidate peak values an overall peak amplitude may reliably be determined.

In particular, by dividing the peak detection window into sub-windows it may become possible to identify those sub-windows which may lie too early in an atrial detection window and which hence may be too close to a preceding T wave, or which may be too late in an atrial detection window and which may hence be too close to a succeeding QRS wave form relating to ventricular activity. Sub-windows which may likely yield incorrect results may be declare invalid and discarded, such that the computation of the peak amplitude may be improved by using only the sub-windows which are declared valid. Valid sub-windows may be all those that are not discarded due to being close to T or QRS.

The sensor arrangement in particular may be formed by an electrode arrangement of one or multiple electrodes arranged on the body. Hence, by means of the sensor arrangement electrical signals may be received, such electrical signals representing intracardiac electrogram recordings and hence being indicative of cardiac activity.

In another embodiment, the sensor arrangement may be configured for sensing cardiac sense signals in the shape of pressure signals, acoustic signals, ultrasound signals, motion signals, and/or impedance signals.

In one embodiment, the body of the implantable medical device may be formed by a lead which is connectable to a generator of the implantable medical device. In this case, the generator may be implanted into a patient, for example subcutaneously remote from the heart, the lead forming the body extending from the generator into the heart such that the body with the sensor arrangement arranged thereon is placed in the heart, for example within the right ventricle in order to engage with tissue at the right ventricle.

In another embodiment, the body may be formed by a housing of a leadless pacemaker device. In this case, the implantable medical device is formed as a leadless device, which does not comprise leads extending from a location outside of the heart into the heart for providing for stimulation and/or sensing within the heart. The housing of the leadless pacemaker device may be placed on tissue with a distal end formed by the housing, the sensor arrangement, e.g., being placed (at least in part) on or in the vicinity of the distal end and engaging with tissue when placing the leadless pacemaker device on tissue with its distal end.

If the implantable medical device is a leadless pacemaker device, the housing provides for an encapsulation of the implantable medical device, the implantable medical device including all required components for autonomous operation, such as the processing circuitry, an energy storage such as a battery, electric and electronic circuitry and the like, within the housing. The housing is fluid-tight such that the implantable medical device may be implanted into cardiac tissue and may be kept in cardiac tissue over an extended period of time to provide for a long-term, continuous cardiac pacing operation.

In one embodiment, the processing circuitry is configured to detect a signal deflection in the cardiac sense signal potentially indicative of an atrial event based on a comparison of the cardiac sense signal to a sense threshold. If it is found that the cardiac sense signal crosses the sense threshold, an atrial event may be identified, and based on the atrial event the peak detection window may be started. The sense threshold herein may be set based on prior peak amplitudes in prior cardiac cycles.

In one embodiment, the candidate peak value of a sub-window corresponds to the maximum of the cardiac sense signal in the sub-window. Hence, within a sub-window the cardiac sense signal is tracked, and the candidate peak value is set to the maximum of the sense signal within the sub-window. This is repeated for all sub-windows, and based on the candidate peak values of all (valid) sub-windows the overall peak amplitude may be determined, for example by setting the peak amplitude to the maximum of the candidate peak values of all (valid) sub-windows. Sub-windows which are discarded due to suspicion of contamination from near-field ventricular activity are considered invalid, while all sub-windows included in the peak amplitude calculation are considered valid.

Thus, a sub-window (i.e., at least one sub-window) may be considered as a valid sub-window, if this sub-window is not discarded due to being close to T or QRS and/or not discarded due to suspicion of contamination from near-field ventricular activity. Accordingly, a candidate peak value (i.e., at least one candidate peak value) may be considered as a valid candidate peak value, if the candidate peak value is in a valid sub-window.

In one embodiment, the processing circuitry is configured to start, at the end of one sub-window, another sub-window. Hence, the length of the peak detection window possibly is initially not fixed, but the length of the overall peak detection window is adaptive in that one sub-window is followed by the next sub-window until no further tracking of the cardiac sense signal for determining the peak amplitude shall be performed. The sub-windows herein are consecutive, such that one sub-window is followed by the next sub-window without a gap, such that a continuous peak detection window is formed by a multiplicity of consecutive sub-windows.

In one embodiment, the processing circuitry is configured to detect a signal deflection in the cardiac sense signal potentially indicative of an atrial event within an atrial detection window. For processing cardiac sense signals for detecting atrial events a windowing scheme may be employed. In particular, signal portions in which likely signal deflections may occur which relate to a ventricular activity (such as a T wave or a QRS waveform in an intracardiac electrogram signal) may be blanked out by applying a blanking window, such that only those portions of the cardiac sense signal are processed in which likely signal deflections relating to atrial activity occur and which are not corrupted by signals not relating to atrial activity. Hence, an atrial detection window is defined, wherein only within the atrial detection window is it searched for signal deflections relating to atrial activity, and an atrial event is identified based on, e.g., a crossing of a sense threshold by the cardiac sense signal.

The atrial detection window may be started at a predefined time duration with respect to a prior ventricular event. Alternatively, the atrial detection window may be adaptively started based on, for example an analysis of the cardiac sense signal and the identification of a waveform prior to an atrial signal deflection, for example a T wave in an intracardiac electrogram. The atrial detection window may be ended after a fixed duration with respect to the prior ventricular event. Alternatively, the atrial detection window duration may be dynamic, for example with a fixed duration relative to the dynamic start of the atrial detection window, or alternatively may be adaptive and extend until the following ventricular event.

For example, the start of the atrial detection window may be set based on comparing the cardiac sense signal to a start threshold. The start threshold may have the same value as the sense threshold which subsequently is used to detect an atrial event, or may have a different value. By monitoring whether the cardiac sense signal crosses the start threshold, in particular becomes smaller than the start threshold, it may be identified that a prior waveform, such as a prior T wave, has ended and hence the atrial detection window may be started to detect an atrial event.

To reliably detect the end of a prior waveform, it may be identified whether a predefined number of signal values are below the start threshold, for example a number in between one to twenty, for example four signal sample values. The signal values may have to be consecutive, or may not have to be consecutive. By identifying whether the pre-required number of signal values are lower than the start threshold, it is identified whether a prior waveform has ended, such that the atrial detection window may be started to search for signal deflections potentially relating to an atrial event.

The peak detection window may have an overall length which, from the time of the detection of an atrial event, covers substantially the entire remaining portion of the atrial detection window. For this, at the end of each sub-window another sub-window may be started until the end of the atrial detection window is reached. In particular, an additional sub-window is added as long as the atrial detection window has not yet expired. If a (last) sub-window exceeds the atrial event detection window, the sub-window may nevertheless be regarded and a candidate peak value may be determined for that sub-window based on a tracking of the cardiac sense signal within the portion of the sub-window in which the atrial detection window has not yet lapsed.

In one embodiment, the processing circuitry is configured to detect a signal deflection indicative of a ventricular event caused by ventricular activity succeeding the atrial event, and to define an exclusion interval based on the ventricular event. In particular, at the time of identifying the ventricular event, the exclusion interval may be set to correspond to a time interval immediately prior to the ventricular event. It then may be identified whether one or multiple of the sub-windows are covered by or reach into the exclusion interval, in which case the sub-windows are discarded and candidate peak values determined for those sub-windows are not regarded when determining the overall peak amplitude.

In particular, the processing circuitry may be configured to exclude a candidate peak value obtained in a sub-window which at least partially overlaps with the exclusion interval. This may be the case for one or multiple sub-windows, such that candidate peak values for one or multiple sub-windows may be discarded when determining the overall peak amplitude.

The length of or limits for any one of the atrial detection window, the peak detection window, the sub-window and the exclusion interval may be programmable.

In one embodiment, the exclusion interval has a first length, and each sub-window has a second length corresponding to 1/Z times the first length, wherein Z is a natural number equal to or larger than 1. Hence, Z sub-windows fit into the exclusion interval.

For example, at least some of the sub-windows may have a length between 3 ms and 100 ms, for example between 12 ms and 35 ms. Herein, all sub-windows may have the same length, or the length of the different sub-windows may differ. For example, the length of the sub-windows may steadily increase or decrease.

Based on a scheme as described herein the peak amplitude may be determined for an atrial event in a reliable and precise manner. The peak amplitude herein may be determined regardless of whether the atrial event has been identified correctly or not. In particular, even in a case in which an atrial event has been erroneously identified, for example due to a signal deflection from a preceding T wave, the peak amplitude associated with an actual peak related to the actual subsequent atrial event may be determined correctly based on the signal tracking within the different sub-windows.

Using the peak amplitude, the processing circuitry may be configured to compute the sense threshold for detecting an atrial event in a subsequent cardiac cycle. In particular, the processing circuitry may be configured to update the sense threshold using an average threshold reference and a percentage ratio according to the formula $$ST = PC \bullet ATR(t),$$

where ST is the current sense threshold, PC is a percentage ratio, and ATR(t) is the current average threshold reference for cycle t. The percentage ratio may lie, for example, in the range between 0% and 100% and may be programmable.

In another embodiment, the average threshold reference may be computed based on the peak amplitude PA according to the following equation:

$$ATR(t) = W \cdot PA(t-1) + (1-W) \cdot ATR(t-1),$$

where W indicates the update weight which determines how much the average threshold reference should change based on the previous peak amplitude, PA(t−1) is the peak amplitude as determined for the previous cycle t−1, and ATR(t−1) is the previous average threshold reference. For the actual cycle t the average threshold reference hence is determined based on the peak amplitude PA determined for that cycle t and based on the previously valid average threshold reference at cycle t−1. For each cycle for which an atrial event As is detected, hence, the average threshold reference is updated and computed anew, such that the average threshold reference is dynamically adjusted on a cycle-by-cycle basis.

The average threshold reference may, for example, be computed as a mean value of peak amplitudes for a predefined number of cardiac cycles in which atrial events have been detected, for example a number in between two to six cardiac cycles, for example four cardiac cycles.

In one embodiment, the processing circuitry comprises a first processing channel having a first gain for processing a first processing signal derived from sensor signals received via the sensor arrangement and a second processing channel having a second gain for processing a second processing signal derived from sensor signals received via the sensor arrangement, the second gain being higher than the first gain.

Generally, the implantable medical device may be configured to process different processing signals. For obtaining such processing signals, a sensor arrangement is provided, the sensor arrangement comprising, e.g., one or multiple electrodes to receive electrical signals from which the processing signals are derived. The processing signals herein, for example, may be obtained each using a pair of electrodes, wherein for obtaining the different processing signals the same pair of electrodes or different pairs of electrodes may be used. In the first case, a single electrical signal, such as an intracardiac electrogram, may be obtained, from which different processing signals, namely the first processing signal and the second processing signal are derived for separate processing. In the latter case, separate electrical signals relating, for example to a ventricular sensing signal and an atrial sensing signal (i.e., by applying a sensing optimized for atrial sensing) may be received in order to derive the first processing signal and the second processing signal from such different electrical signals, the different electrical signals, for example being received using different pairs of electrodes of the sensor arrangement.

The different processing signals, in one embodiment, are processed in different processing paths of the processing circuitry. For this, the processing circuitry comprises a first processing channel for processing the first processing signal, the first processing signal relating, for example to a near-field (in particular ventricular) sensing signal which, according to the placement of the implantable medical device, for example in a ventricle of a patient's heart, may be large such that the first processing channel may exhibit a rather low gain.

In addition, the processing circuitry comprises a second processing channel for processing the second processing signal, which may relate, for example, to a far-field atrial sensing signal which, in case of a placement of the implantable medical device in the ventricle, may have a small amplitude, due to the distance between the location of implantation and the source of origin of the signals. In order to allow for a reliable processing of the second processing signal, the second processing channel exhibits a gain higher than the gain of the first processing channel, such that features relating to atrial activity may be suitably analyzed within the received signals.

Because, for a placement of the implantable medical device in, for example, the ventricle, atrial activity occurs in the far-field, atrial events within a regular ventricular sensing signal (for example, obtained from a regular ventricular QRS sensing channel) may be hard to discern, as a P wave stemming from atrial activity may exhibit a small amplitude in relation to QRS and T waves. For this reason signal portions relating to far-field activity may be processed separately from signals relating to near-field activity within the second processing channel, such that within the second processing channel far-field events may be detected with increased reliability and enhanced timing precision.

The implantable medical device, in one aspect, is to be placed entirely or partially in the right or left ventricle.

In one aspect, the sensor arrangement is formed by an electrode arrangement, the electrode arrangement comprising a first electrode arranged in the vicinity of a tip of the body. The first electrode shall come to rest on cardiac tissue in an implanted state of the implantable medical device, such that the first electrode contacts cardiac tissue, e.g., at a location effective for injecting a stimulating signal into cardiac tissue for provoking a pacing action, in particular a ventricular pacing.

In one aspect, the electrode arrangement comprises a second electrode formed by an electrode ring circumferentially extending about the body. Alternatively, the second electrode may, for example, be formed by a patch or another electrically conductive area formed on the body. The second electrode is placed at a distance from the tip of the body and hence at a distance from the first electrode arranged at the tip.

In one embodiment, the processing circuitry is configured to process, as said first processing signal, a first signal sensed between the first electrode and the second electrode. Such first signal may be denoted as near-field vector to be received between a pair of electrodes comprised of the first electrode and the second electrode. As the first electrode and the second electrode may, in one embodiment, be located at a rather close distance to each other, such pair of electrodes is predominantly suited to receive signals in close proximity to the implantable medical device, i.e., in the near-field region within the ventricle if the implantable medical device is implanted into the ventricle. The sense signal received in between the first electrode and the second electrode is provided to the first processing channel for processing in order to, for example, detect near-field (e.g., ventricular) events in the signal.

In one embodiment, the body comprises a remote location (e.g., the far end of a housing of a leadless pacemaker device) removed from the tip, the electrode arrangement comprising a third electrode arranged on the body at the remote location. The third electrode is operatively connected to the processing circuitry, such that the processing circuitry is enabled to receive and process signals received via the third electrode.

In one aspect, the processing circuitry is configured to process, as said second processing signal, a second signal sensed between the first electrode and the third electrode. Such second signal vector arising between the first electrode and the third electrode may be referred to as far-field vector, the first electrode and the third electrode exhibiting a distance with respect to each other larger than the first and the second electrode. The second signal may in particular be processed to detect events in the far-field, i.e., atrial contractions in case the implantable medical device is placed in the ventricle, such that by means of the second signal an intrinsic atrial activity prior to injecting a pacing stimulus may be captured.

The second signal sensed between the first electrode and the third electrode may be used to sense intrinsic atrial contractions in order to provide for an atrial-to-ventricular synchronization by timely injecting a stimulus at the ventricular location of implantation of the pacemaker device following atrial contractions. The second signal is provided to the second processing channel in order to process the signal and detect atrial events from the signal, in order to provide for a pacing action based on detected atrial events, hence allowing for ventricular pacing under atrioventricular (AV) synchrony.

In one embodiment, the second processing channel comprises a processing stage for differentiating one wave portion from another wave portion in the second processing signal. The processing stage in particular may be configured to apply, to the second processing signal, at least one of a bandpass filtering, a blanking window for excluding a portion of the second sensor signal from further processing, a moving average filtering, and a rectification. By means of the processing stage, in particular such wave portions shall be isolated and/or emphasized within the signal to be processed which may be indicative of, e.g., an atrial event. If the implantable medical device is placed in the ventricle of a patient's heart, signal portions relating to far-field atrial activity may have a much smaller amplitude than signal portions relating to a near-field ventricular activity. Hence, the processing serves to differentiate between the different signal portions in order to identify such signal portion which may contain signals relating to far-field atrial activity.

For isolating, e.g., the P wave in an intracardiac electrogram, a bandpass filtering may be applied, hence differentiating wave portions relating to the P wave from wave portions in particular relating to QRS and T waves stemming from ventricular activity. Alternatively or in addition, a blanking method may be applied in order to blank out certain portions of the second processing signal, namely such portions which contain signals stemming from events other than a far-field atrial activity. A blanking window, for this, serves to silence signal portions which are not of interest for far-field activity, but which may rather interfere with the detection of far-field activity. By means of a blanking window such portions of the signal which do not relate to far-field atrial activity hence are excluded from processing, such that the processing is limited to those signal portions (likely) relating to far-field activity. Alternatively or in addition, other methods such as a moving average filtering, finite differences or a rectification of the signal may be applied. A moving averaging filter herein can be used to smooth the processing signal. Rectification can serve to easily compare the processed signal to a (single) threshold in order to identify when the signal magnitude exceeds a predefined threshold.

In another aspect, a method for operating an implantable medical device for providing for an intracardiac function comprises: receiving, using a sensor arrangement arranged on a body of the implantable medical device, cardiac sense signals; and processing, using a processing circuitry operatively connected to the sensor arrangement, cardiac sense signals received using the sensor arrangement to detect, in a cardiac cycle, a first atrial event candidate based on a comparison of the cardiac sense signal with a sense threshold, to determine a modified sense threshold, to monitor, by comparing the cardiac sense signal to said modified sense threshold following the detection of the first atrial event candidate, whether in the same cardiac cycle a second atrial event candidate is detected.

The advantages and advantageous embodiment described above for the device equally apply also to the method, such that is shall be referred to the above.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein.

DETAILED DESCRIPTION

Figure 1:
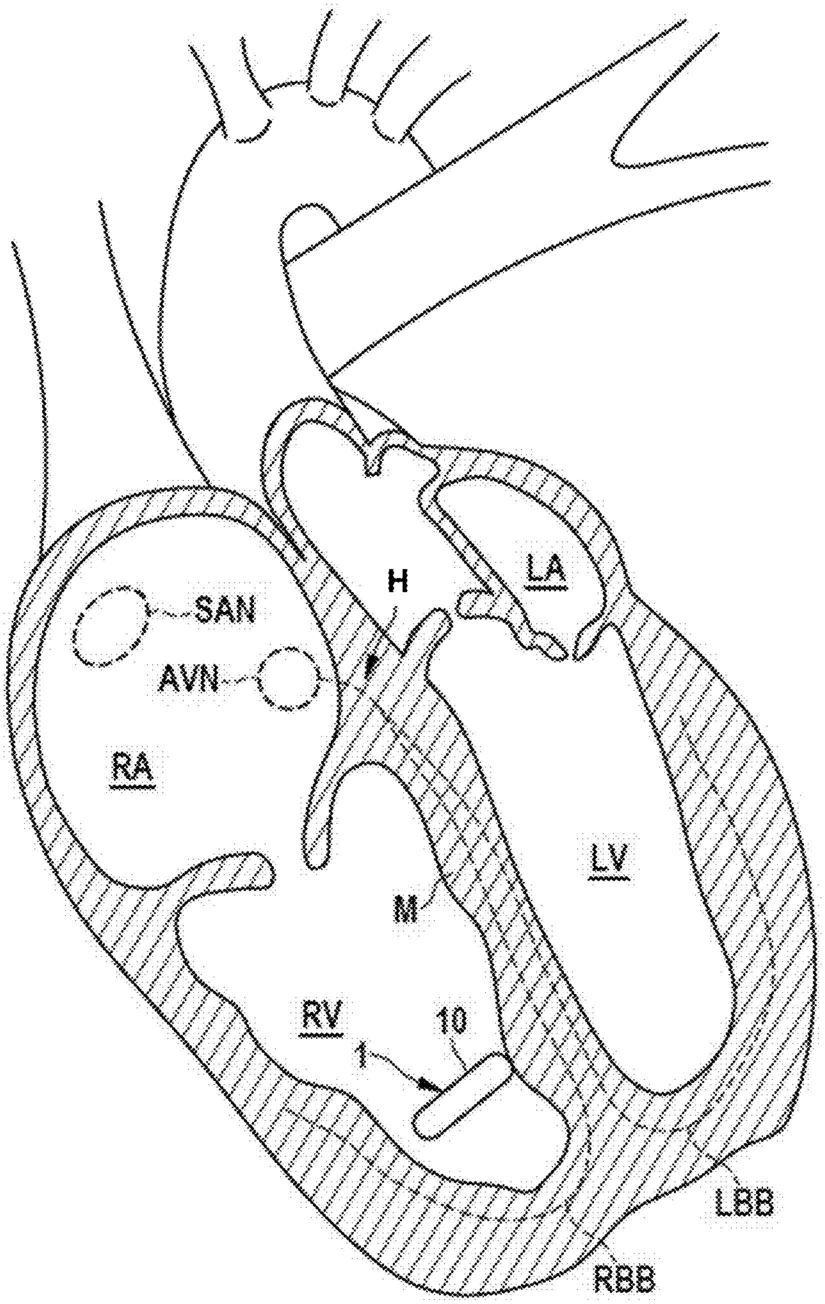
FIG. 1 shows a schematic view of the human heart, with an implantable medical device in the shape of a leadless pacemaker device implanted therein.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

In the present invention it is proposed to provide an implantable medical device providing for an intracardiac function, in particular ventricular pacing, specifically so-called VDD pacing.

FIG. 1 shows, in a schematic drawing, the human heart comprising the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle His extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In case of a block at the atrioventricular node AVN, the intrinsic electrical conduction system of the heart H may be disrupted, causing a potentially insufficient intrinsic stimulation of ventricular activity, i.e., insufficient or irregular contractions of the right and/or left ventricle RV, LV. In such a case, a pacing of ventricular activity by means of a pacemaker device may be indicated, such pacemaker device stimulating ventricular activity by injecting stimulation energy into intracardiac tissue, specifically myocardium M.

In one embodiment, an implantable medical device 1 in the shape of a leadless cardiac pacemaker device, as schematically indicated in FIG. 1, is provided for a ventricular pacing action, the leadless pacemaker device having a body 10 formed by the housing of the leadless pacemaker device.

Figure 7:
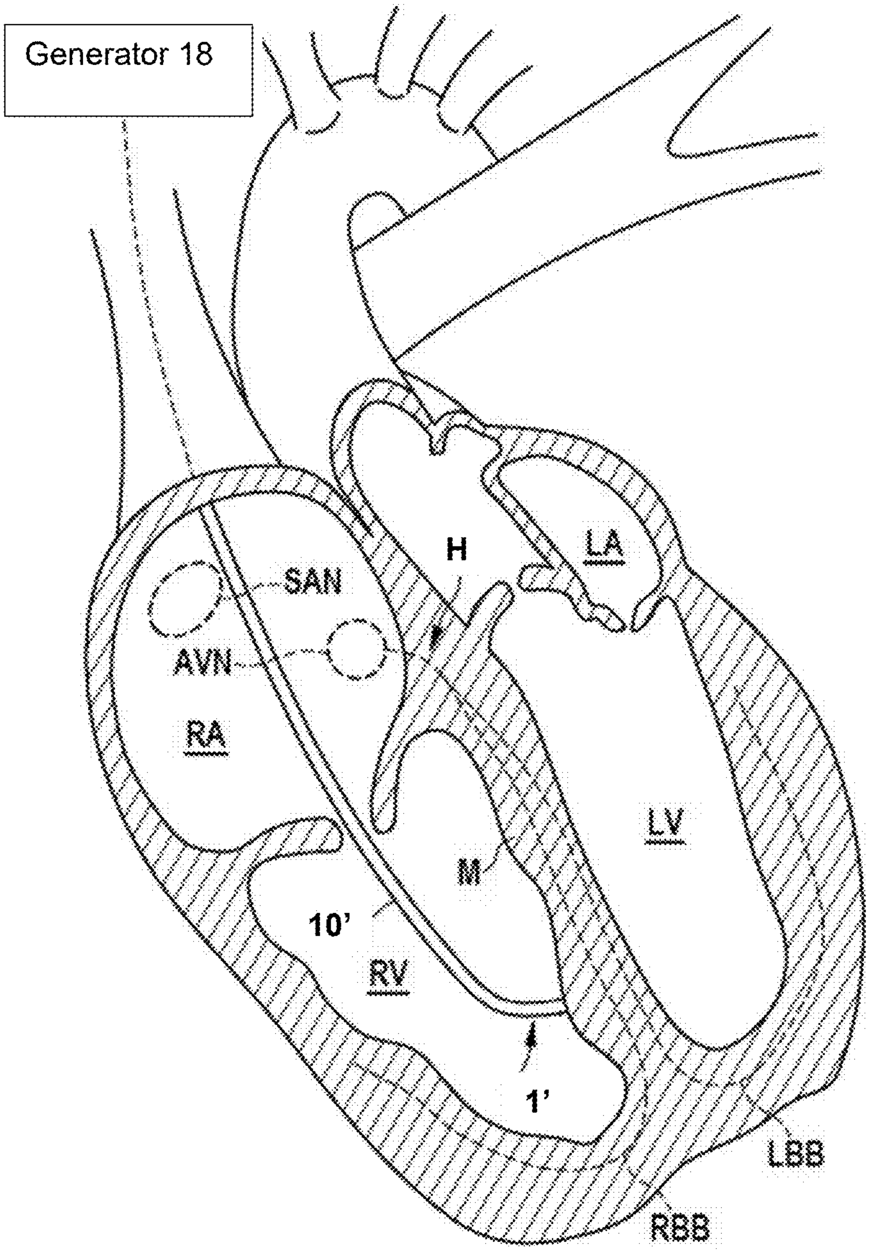
FIG. 7 shows a schematic view of the human heart, with an implantable medical device in the shape of cardiac stimulation device having a lead implanted in the right ventricle.

In another embodiment, as shown in FIG. 7, the implantable medical device 1' may be a stimulation device having a generator 18 and at least one lead forming a body 10' of the implantable medical device 1' and extending transvenously from the generator 18 into the patient's heart.

Whereas common implantable medical devices are designed to sense a ventricular activity by receiving electrical signals from the ventricle RV, LV they are placed in, it may be desirable to provide for a pacing action which achieves atrioventricular (AV) synchrony by providing a pacing in the ventricle in synchrony with an intrinsic atrial activity. For such pacing mode, also denoted as VDD pacing mode, it is required to sense atrial activity and identify atrial events relating to atrial contractions in order to base a ventricular pacing on such atrial events.

Figure 3:
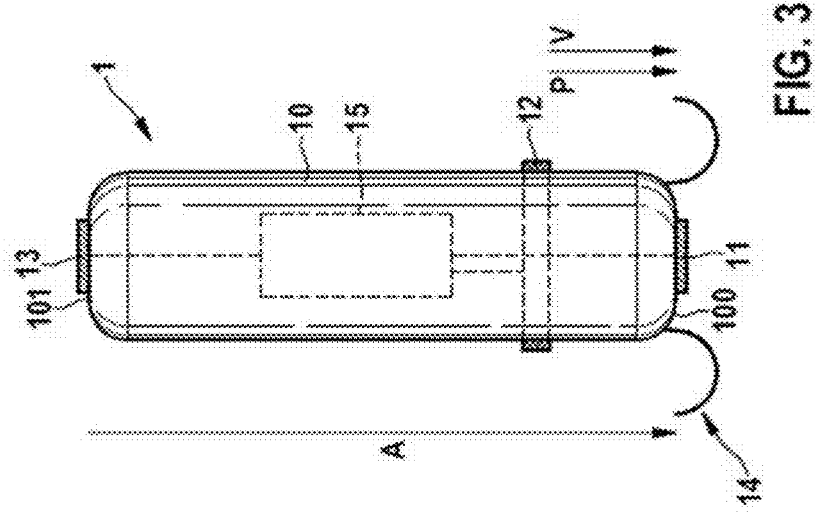
FIG. 3 shows a schematic view of an implantable medical device, indicating signal vectors between different electrodes of the implantable medical device.
Figure 2:
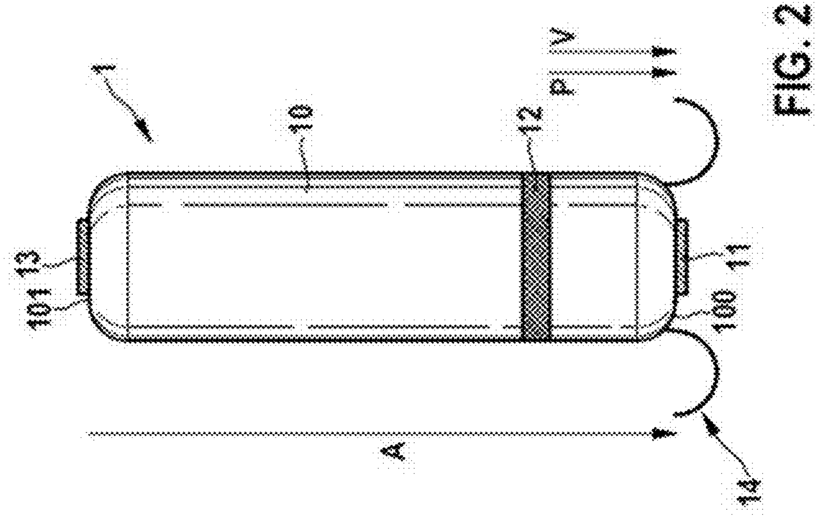
FIG. 2 shows a schematic view of an implantable medical device.

Referring now to FIGS. 2 and 3, in one embodiment an implantable medical device 1 in the shape of a leadless pacemaker device configured to provide for intracardiac pacing, in particular in a VDD pacing mode, comprises a housing 10 enclosing electrical and electronic components for operating the implantable medical device 1. In particular, enclosed within the housing 10 is a processing circuitry 15, comprising, for example, also a communication interface for communicating with an external device, such as a programmer wand. In addition, electrical and electronic components such as an energy storage in the shape of a battery are confined in the housing 10. The housing 10 provides for an encapsulation of components received therein, the housing 10 having the shape of, e.g., a cylindrical shaft having a length of, for example, a few centimeters.

The implantable medical device 1 is to be implanted immediately on intracardiac tissue M. For this, the implantable medical device 1 comprises, in the region of a tip 100, a fixation device 14, for example in the shape of nitinol wires to engage with intracardiac tissue M for fixedly holding the implantable medical device 1 on the tissue in an implanted state.

The implantable medical device 1 in the embodiment of FIGS. 2 and 3 does not comprise leads, but receives signals relating to a cardiac activity by means of an electrode arrangement arranged on the housing 10 and also emits stimulation signals by means of such electrode arrangement. In the embodiment of FIGS. 2 and 3, the implantable medical device 1 comprises different electrodes 11, 12, 13 making up the electrode arrangement and serving to emit pacing signals towards intracardiac tissue M for providing a pacing and to sense electrical signals indicative of a cardiac activity, in particular indicative of atrial and ventricular contractions.

A first electrode 11 herein is denoted as pacing electrode. The first electrode 11 is placed at a tip 100 of the housing 10 and is configured to engage with cardiac tissue M.

A second electrode 12 herein is denoted as pacing ring. The second electrode 12 serves as a counter-electrode for the first electrode 11, a signal vector P arising between the first electrode 11 and the second electrode 12 providing for a pacing vector P for emitting pacing signals towards the intracardiac tissue M.

In addition, the second electrode 12 serves as a sensing electrode for sensing signals, in particular relating to ventricular contractions, a signal vector V arising between the second electrode 12 and the first electrode 11, the signal vector V being denoted as near-field vector.

The second electrode 12 is placed at a distance from the first electrode 11 and, for example, has the shape of a ring extending circumferentially about the housing 10. The second electrode 12 is, for example, placed at a distance of about 1 cm from the tip 100 of the housing 10 at which the first electrode 11 is placed.

The implantable medical device 1, in the embodiment of FIGS. 2 and 3, in addition comprises a third electrode 13 placed at a far end 101 of the housing 10, the third electrode 13 serving as a sensing electrode for sensing signals indicative of cardiac activity in the far-field. In particular, a signal vector A arises between the third electrode 13 and the first electrode 11, the signal vector A picking up signals being indicative, for example, of atrial contractions and being denoted as far-field vector.

The electrodes 11, 12, 13 are in operative connection with the processing circuitry 15, the processing circuitry 15 being configured to cause the first electrode 11 and the second electrode 12 to emit a pacing signal for providing a stimulation at the ventricle. The processing circuitry 15 furthermore is configured to process signals received via the electrodes 11, 12, 13 to provide for a sensing of cardiac activity, in particular atrial and ventricular contractions.

If the implantable medical device 1' has the shape of a stimulation device comprising a generator 18 and a lead extending from the generator 18, as shown in the embodiment of FIG. 7, a similar electrode arrangement comprising, for example, three electrodes 11, 12, 13 may be arranged on a lead implanted in and extending into the right ventricle RV, as shown in FIG. 7, such that the above also applies to an embodiment of the implantable medical device 1' having a lead extending into the patient's heart. In this case, the processing circuitry 15 may be part of the generator 18 and may be in operative connection with an electrode arrangement arranged on the lead.

In order to provide for a pacing in the ventricle in which the implantable medical device 1' is placed, in particular to enable a pacing in the VDD mode, a sensing of atrial activity is required to provide for detected atrial sense markers in order to time a pacing in the ventricle to obtain atrioventricular (AV) synchrony. For this, a far-field signal from in particular the right atrium RA (see FIGS. 1 and 7) shall be sensed in order to allow for synchronous pacing in the right ventricle RV by means of the implantable medical device 1' being implanted on intracardiac tissue M in the right ventricle RV.

Figure 4:
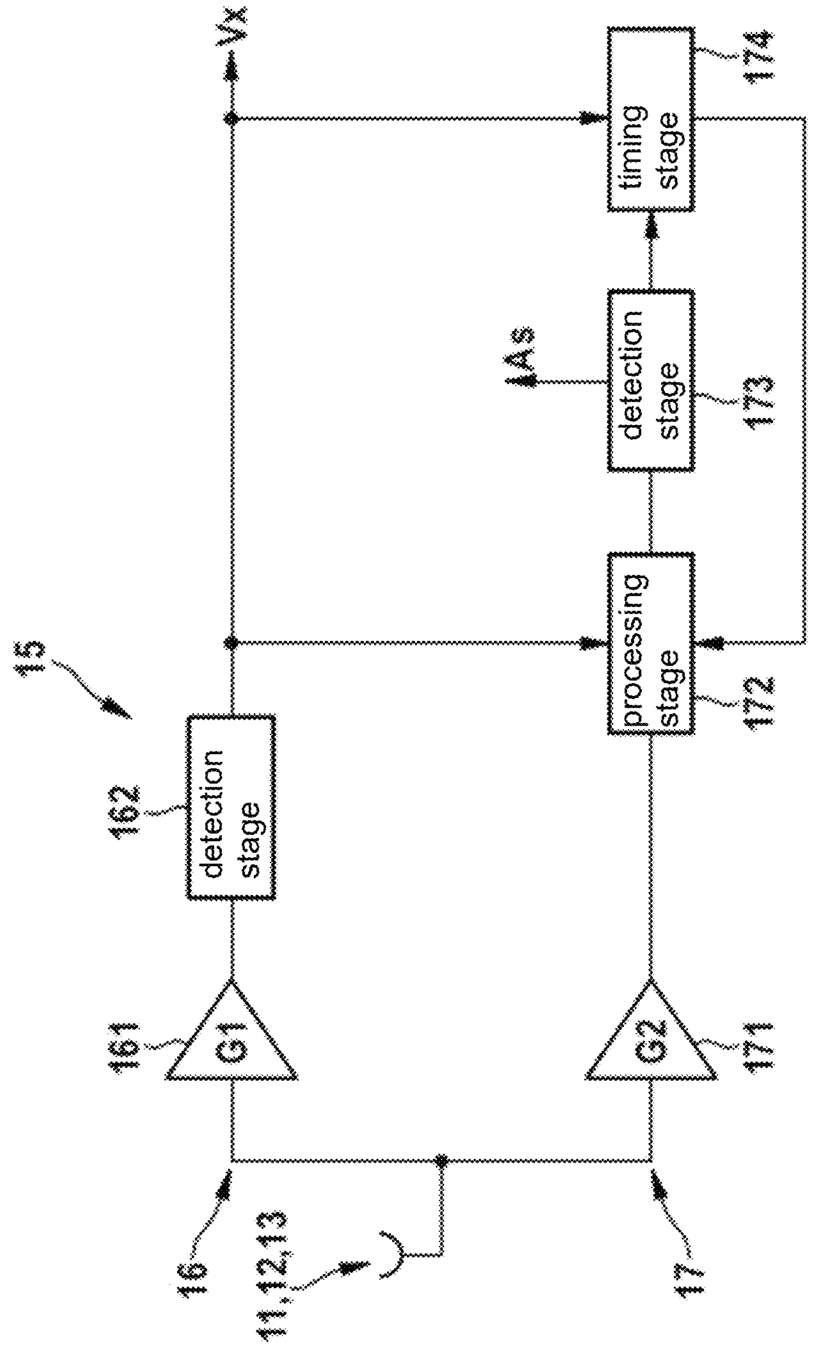
FIG. 4 shows a schematic view of a processing circuitry of an embodiment of an implantable medical device.

Referring now to FIG. 4, the processing circuitry 15 comprises, in one embodiment, two processing channels 16, 17 for processing different processing signals relating to ventricular activity and atrial activity. Herein, typically, an intracardiac electrogram (IEGM) contains a signal portions relating to ventricular activity (in particular a QRS wave) and atrial activity (in particular a P wave), signal portions relating to atrial activity however resulting from a far-field signal source and hence being far less pronounced and having a far smaller amplitude then signal portions relating to a ventricular activity in the near-field, i.e., arising in close proximity to the implanted implantable medical device 1. For this reason, the two processing channels 16, 17 are associated with different gains G1, G2, a first processing channel 16 serving to process a first processing signal to identify ventricular events Vx at a rather low gain G1 and a second processing channel 17 being configured to process a second processing signal to identify atrial events at a significantly higher gain G2.

In particular, the first processing channel 16 is connected to the electrode arrangement comprised of the electrodes 11, 12, 13, the first processing channel 16 being configured in particular to sense and process a signal received via the electrodes 11, 12 (near-field vector V in FIGS. 2 and 3). The first processing channel 16 comprises a first amplification stage 161 having a gain G1, the first amplification stage 161 being followed by a detection stage 162 which is configured to identify ventricular sense markers Vx from the first processing signal processed within the first processing channel 16.

The second processing channel 17 is likewise connected to the electrode arrangement comprised of electrodes 11, 12, 13, wherein the second processing channel 17 may in particular be configured to process a signal sensed via the far-field vector A, that is in between the electrodes 11, 13 placed at the tip 100 and the far end 101 of the housing 10 as illustrated in FIGS. 2 and 3. The second processing channel 17 comprises a second amplification stage 171 having a second gain G2, the second amplification stage 171 being followed by a processing stage 172 and a second detection stage 173.

The processing stage 172 serves to pre-process the second processing signal after amplification. The detection stage 173 in turn serves to evaluate and analyze the processed signal in order to identify atrial events within the second processing signal, the second processing channel 17 then outputting atrial sense markers As indicative of atrial events detected in the processed signal.

In addition, the processing circuitry 15 comprises a timing stage 174 which uses timing information received from the first processing channel 16 and the second processing channel 17 to provide for a pacing timing, in particular a VDD timing for achieving an atrial-ventricular synchronous pacing.

In order to identify and analyze atrial events, the gain G2 of the second processing channel 17 is (significantly) higher than the gain G1 of the first processing channel 16. This generally allows to analyze signal portions relating to atrial events, but makes it necessary to discern such signal portions relating to atrial events from other signal portions, in particular signal portions relating to ventricular events Vx in the near-field and hence being far larger than signal portions originating from atrial events in the far-field.

Within the processing stage 172, for example a bandpass filtering, a windowing (e.g., partial blanking), a smoothing by means of a moving average filtering and a rectification may take place. A first or second order difference may be applied to remove a non-zero baseline while enhancing P wave deflections.

Figure 5A:
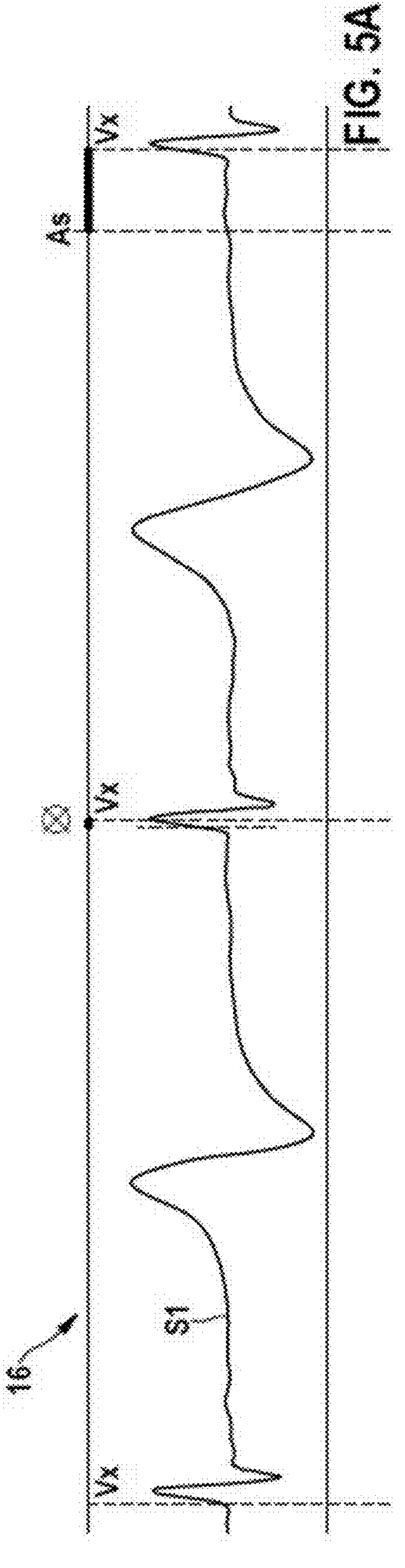
FIG. 5A shows a first processing signal in the shape of an intracardiac electrogram (IEGM) processed by a first processing channel of the processing circuitry.
Figure 5B:
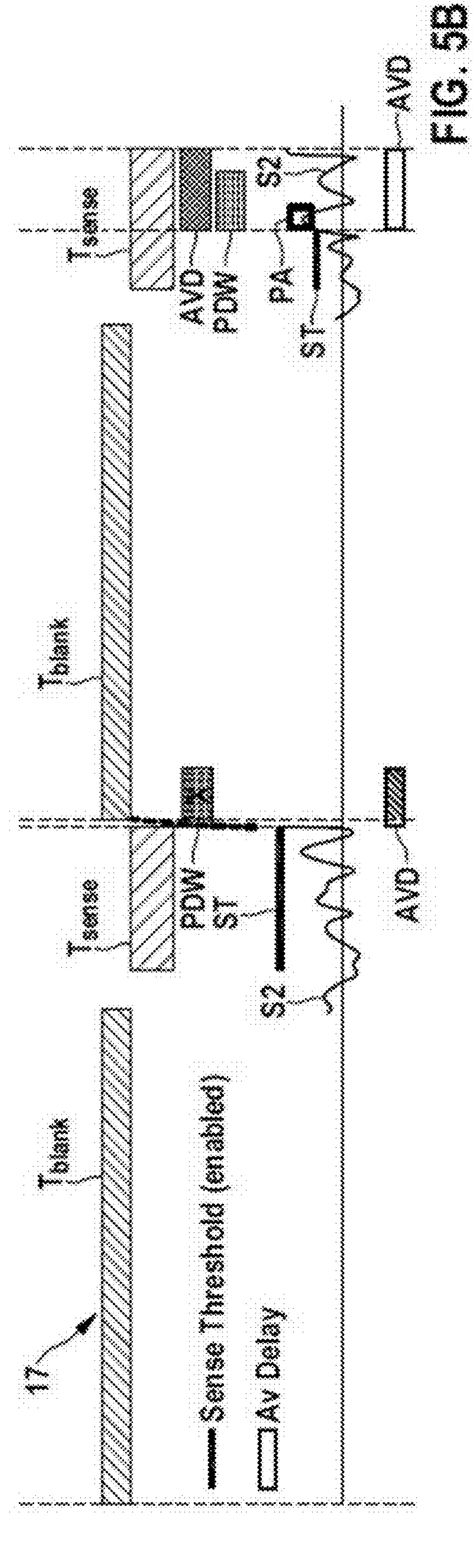
FIG. 5B shows a second processing signal processed by a second processing channel of the processing circuitry.

FIGS. 5A and 5B show examples of signals S1, S2 as processed in the different processing channels 16, 17, FIG. 5A at the top showing a signal S1 as processed by the first processing channel 16 and FIG. 5B at the bottom showing a signal S2 as processed by the second processing channel 17. As a result of the processing, ventricular events Vx and atrial events As are identified and corresponding markers are output.

As apparent from FIG. 5B, the sensing of atrial events As uses a windowing scheme, employing in particular a blanking window $T_{blank}$ for blanking out signal portions of the signal S2 potentially relating to ventricular activity.

In particular, by means of the detection of ventricular events Vx in the first processing channel 16 a timing in between atrial events As and ventricular events Vx may be determined. According to such timing a start point and an end point of the blanking window $T_{blank}$ may be set, hence excluding signal portions from the processing which do not relate to atrial activity. Large ventricular signals in this way may be suppressed such that signal portions relating to a ventricular activity may not interfere with a detection of atrial events.

During the blanking window $T_{blank}$, the second processing channel 17 may be turned off. In particular, the amplification stage 171 of the second processing channel 17 may be switched of in order to save power.

Generally, a detection for atrial events As takes place outside of the blanking window $T_{blank}$. Herein, a detection window $T_{sense}$ for detecting atrial events may start at the end of a prior blanking window $T_{blank}$. Alternatively, a detection window $T_{sense}$ may—as shown in the embodiment of FIG. 5B—have a delay with respect to the end of a prior blanking window $T_{blank}$, such that a signal processing within the second processing channel 17 starts at the end of a prior blanking window $T_{blank}$, a detection for atrial events As however starting only after a certain delay.

Generally, an atrial event As is assumed to be present if, in the detection window $T_{sense}$, the signal S2 crosses a sense threshold ST, as it is shown in FIG. 5B. The comparison may take place based on a rectification of the sense signal S2. Alternatively, a positive and negative sense threshold ST may be used, which may have the same value or may differ in their values. A threshold crossing herein may be assumed if one signal value is larger than the sense threshold ST. Alternatively, a crossing of the sense threshold ST is assumed if a predefined number of signal values are larger than the sense threshold ST, for example two or more consecutive or non-consecutive (total) sample values.

Generally, if an atrial event As is detected, as it is the case for the second cardiac cycle in FIG. 5B, the atrial event As is used for a further processing, in particular to update the sense threshold ST and to achieve an atrial-ventricular synchronous pacing.

In particular, the atrial event As is taken as that point in time at which a crossing of the sense threshold ST is identified. At the time of the atrial event As a peak detection window PDW starts, and based on data recorded during that peak detection window PDW a peak amplitude PA is determined as the maximum signal value within the peak detection window PDW. This is indicated in FIG. 5B for the second cycle at the right.

Also, in case of a detection of an atrial event As, an atrial-ventricular delay AVD may be determined and used for subsequent processing. If no ventricular event Vx is detected after lapse of the atrial-ventricular delay AVD, a pacing signal may be injected to cause a ventricular stimulation.

As it is shown in FIG. 5B, the peak amplitude PA is generally determined within a peak detection window PDW following the detection of an atrial event As. Generally, the peak amplitude PA herein is determined by tracking the sense signal S2 and by in this way identifying the maximum of the sense signal S2 in the peak detection window PDW. The PDW in the first cycle of FIG. 5B is disqualified because of its close proximity to the ventricular event. This concept is explained more in FIG. 6.

Figure 6:
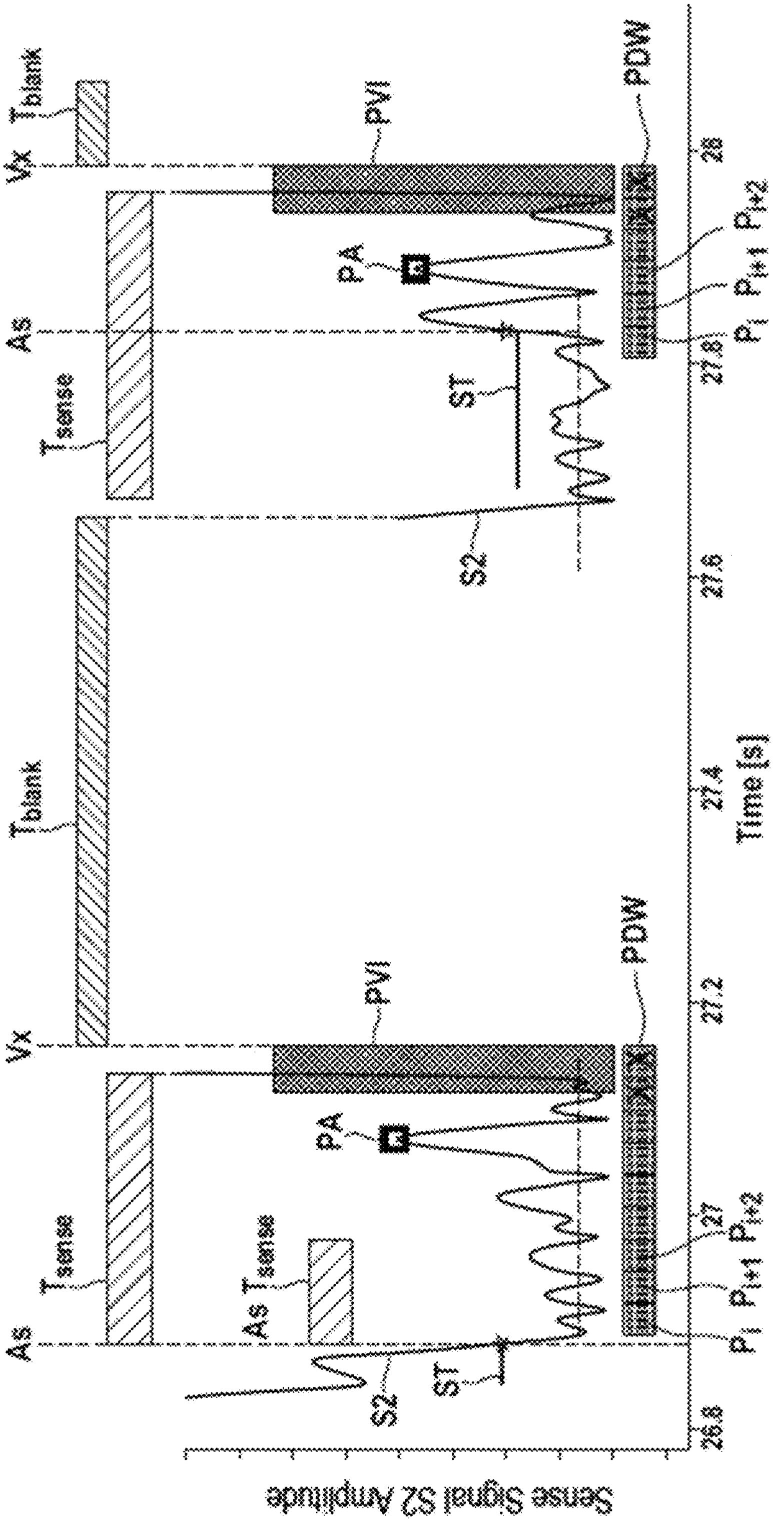
FIG. 6 shows an example of a second processing signal within two cardiac cycles.

Referring now to FIG. 6, there may be scenarios in which an atrial event As is incorrectly determined at a point of time within a cardiac cycle prior to the actual atrial event, as this is shown for one cardiac cycle in FIG. 6 on the left. This may be the case if, for example, the end of a prior signal waveform, such as a T wave in an intracardiac electrogram signal, reaches into the atrial detection window $T_{sense}$, such that at the immediate beginning of the atrial detection window $T_{sense}$ a crossing of the sense threshold ST is identified and hence an atrial event As is (incorrectly) detected. In this case, if the peak detection window PDW would be too short, it would be impossible to correctly determine the peak amplitude PA associated with the actual atrial event As following (much) later than the erroneously identified atrial event As.

In another scenario, shown in the cardiac cycle in FIG. 6 on the right, an atrial event As may be determined correctly by identifying a crossing of the sense threshold ST by the sense signal S2. The actual atrial event As, however, may lie close to a subsequent ventricular event Vx, such that the signal deflections associated with the atrial event As may be corrupted with signal deflections associated with the subsequent ventricular event Vx. If in this case the peak detection window PDW is too long and reaches into the region of the subsequent ventricular activity, the peak amplitude PA again may be determined incorrectly due to the signal corruption by the subsequent ventricular signal deflections.

For this reason, according to one embodiment a scheme is proposed in which the peak detection window PDW is divided into a multiplicity of sub-windows $P_i$, $P_{i+1}$, . . . the signal processing for determining the peak amplitude PA taking place in the separate sub-windows $P_i$, $P_{i+1}$, . . . .

The peak detection window PDW generally is started at the time of detection of the atrial event As, as it is the case for both the cardiac cycle as shown on the left and the cardiac cycle shown on the right in FIG. 6. Hence, at the time of the detection of the atrial event As, a sub-window is started, and at the end of the sub-window another sub-window is started, which is repeated until the end of the atrial detection window $T_{sense}$ is reached. Hence, following the detection of an atrial event As the peak detection window PDW essentially covers the entire remaining portion of the atrial detection window $T_{sense}$.

Herein, in each sub-window $P_i$, $P_{i+1}$, . . . a candidate peak value is determined by tracking the signal S2 in the sub-window $P_i$, $P_{i+1}$, . . . and by setting the candidate peak value according to the maximum of the sense signal S2 in the respective sub-window $P_i$, $P_{i+1}$, . . . . To determine the peak amplitude PA, then, the maximum of all candidate peak values of all (valid) sub-windows $P_i$, $P_{i+1}$, . . . is determined, and the peak amplitude PA is set to that maximum.

As visible from FIG. 6, one or multiple sub-windows $P_i$, $P_{i+1}$, . . . may fully or partially overlap with an exclusion interval PVI as it is defined prior to a ventricular event Vx. Namely, if subsequent to the detection of an atrial event As a ventricular event Vx is identified (which may be an intrinsic event or may be a paced event), an exclusion interval PVI (also denoted as pre-Vx interval) is defined, the exclusion interval PVI defining a time span immediately prior to the ventricular event Vx such that the exclusion interval PVI ends with the ventricular event Vx.

The exclusion interval PVI in particular may be defined in order to exclude an atrial event As which lies too close to the subsequent ventricular event Vx. In addition, the exclusion interval PVI is defined to exclude sub-windows $P_i$, $P_{i+1}$, . . . of the peak detection window PDW which at least partially overlap with the exclusion interval PVI. If a sub-window $P_i$, $P_{i+1}$, . . . is excluded, a candidate peak value determined for that sub-window $P_i$, $P_{i+1}$, . . . is not used for determining the overall peak amplitude PA. The PDW sub-windows that are disqualified because of overlap with the exclusion interval PVI are marked with an 'X' in FIG. 6.

The duration of the atrial detection window $T_{sense}$ may be programmable.

Likewise, the duration of the exclusion interval PVI may be programmable.

The duration of the peak detection window PDW may also be programmable, wherein it also is conceivable that the duration of the peak detection window PDW is adaptively set. For example, the peak detection window PDW may be determined by the sequence of sub-windows $P_i$, $P_{i+1}$, . . . wherein the peak detection window PDW ends if a sub-window is started and extends beyond the end of the atrial detection window $T_{sense}$.

The duration of the sub-windows $P_i$, $P_{i+1}$, . . . may be programmable and may, for example, have a value in between 7 ms and 100 ms, for example between 12 ms and 35 ms. The sub-windows may have equal durations, or may differ in their durations.

In one embodiment, a natural number of sub-windows fits into the exclusion interval PVI, such that the lengths of the exclusion interval PVI and the sub-windows are set in dependence on one another.

The peak amplitude PA, in one embodiment, may be used to update the sense threshold ST for the next cardiac cycle.

In particular, the processing circuitry 15 may be configured to update the sense threshold ST using an average threshold reference and a percentage ratio according to the formula $$ST = PC \cdot ATR(t),$$

where ST is the current sense threshold, PC is the percentage ratio, and ATR(t) is the average threshold reference for the current cycle t. The percentage ratio may lie, for example, in the range between 0% and 100%.

The average threshold reference may be determined based on a mean value for a number of previous cardiac cycles in which atrial events have been identified and correspondingly peak amplitude values have been obtained. The average threshold reference in this case, for example, may be determined as the average of the peak amplitude values in the previous cardiac cycles.

In another embodiment, the average threshold reference may be computed based on the peak amplitude PA according to the following equation:

$$ATR(t) = W \cdot PA(t-1) + (1-W) \cdot ATR(t-1),$$

where W indicates the update weight which determines how much the average threshold reference should change based on the previous peak amplitude, PA(t−1) is the peak amplitude as determined for the previous cycle t−1, and ATR(t−1) is the previous average threshold reference. For the actual cycle t the average threshold reference hence is determined based on the peak amplitude PA determined for that cycle t and based on the previously valid average threshold reference at cycle t−1. For each cycle for which an atrial event As is detected, hence, the average threshold reference is updated and computed anew, such that the average threshold reference is dynamically adjusted on a cycle-by-cycle basis.

If no (valid) atrial event As is detected, no peak amplitude PA is determined and the average threshold reference ATR is not updated. In this way it is avoided that a false detection of an atrial event As may cause a false increase of the sense threshold ST and a subsequent capture loss of atrial activity. This is the case for the first cardiac cycle as shown in FIGS. 5A and 5B, in which no crossing of the sense threshold ST is detected and correspondingly no atrial event As is identified.

Using atrial sense markers As output by the processing circuitry 15, a ventricular synchronous pacing may be achieved. For this, it can be detected whether, following a detected atrial sense marker As, an intrinsic ventricular sense marker Vx occurs within a predefined time delay window (corresponding to the atrial-ventricular delay AVD) after the atrial sense marker As, in which case no stimulation is required. If no ventricular sense marker Vx is detected, a stimulation pulse may be emitted, causing a synchronous pacing at the ventricle.

Conversely, also an asynchronous pacing can be performed.

Utilizing a far-field electrical signal received by means of an implantable medical device can offer a superior detection of far-field events, in particular atrial events in case the implantable medical device is implanted into the ventricle. A tracking of far-field events by using and evaluating electrical signals may allow for an increased consistency and reliability in particular with respect to external factors such as posture and patient activity.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1, 1' Implantable medical device
10, 10' Body (housing)
100 Tip

| List of reference numerals | |
|---|---|
| 1' | Implantable medical device |
| 10' | Body (housing) |
| 100 | Tip |
| 101 | Far end |
| 11 | First electrode (pacing electrode) |
| 12 | Second electrode (pacing ring) |
| 13 | Third electrode |
| 14 | Fixation device |

-continued

| List of reference numerals | |
|---|---|
| 15 | Processing circuitry |
| 16 | Processing channel |
| 161 | Amplification stage |
| 162 | Detection stage |
| 17 | Processing channel |
| 171 | Amplification stage |
| 172 | Processing stage |
| 173 | Detection stage |
| 174 | Timing stage |
| 18 | Generator |
| A | Signal vector (atrial/far-field vector) |
| As | Atrial event (atrial sense marker) |
| ATR | Average threshold reference |
| AVD | Atrial-ventricular delay |
| AVN | Atrioventricular node |
| G1, G2 | Gain |
| H | HIS bundle |
| LA | Left atrium |
| LAT | Lower absolute threshold |
| LBB | Left bundle branch |
| LV | Left ventricle |
| M | Intracardiac tissue (myocardium) |
| P | Signal vector (pacing vector) |
| PA | Peak amplitude |
| PDW | Peak detection window |
| PVI | Exclusion interval (pre-Vx interval) |
| $P_i$, $P_{i+1}$ | Sub-window of peak detection window |
| RA | Right atrium |
| RBB | Right bundle branch |
| RV | Right ventricle |
| S1, S2 | Signal |
| SAN | Sinoatrial node |
| ST | Sense threshold |
| $T_{blank}$ | Blanking window |
| $T_{sense}$ | Detection window |
| V | Signal vector (ventricular/near-field vector) |
| Vx | Ventricular event (ventricular sense marker) |

The invention claimed is:

1. An implantable medical device configured to provide for an intracardiac function, the implantable medical device comprising:

a body;

a sensor arrangement arranged on the body and configured to receive a cardiac sense signal; and a processing circuitry operatively connected to the sensor arrangement, wherein the processing circuitry is configured to process the cardiac sense signal received using the sensor arrangement to detect a signal deflection in the cardiac sense signal potentially indicative of an atrial event caused by atrial activity; and to start a peak detection window based on a detection of said signal deflection for determining a peak amplitude associated with said atrial event, wherein the peak detection window (PDW) comprises one or more sub-windows, the processing circuitry being configured to determine a candidate peak value in each sub-window and to set the peak amplitude based on valid candidate peak values of one or more consecutive sub-windows, wherein the valid candidate peak values are candidate peak values in valid sub-windows, and wherein a sub-window is considered valid, if this sub-window is not discarded due to being close to a T or QRS wave and/or not discarded due to suspicion of contamination from near-field ventricular activity.

2. The implantable medical device according to claim 1, wherein the body is formed by a lead which is connectable to a generator of the implantable medical device, or wherein the body is formed by a housing of a leadless pacemaker device.

3. The implantable medical device according to claim 1, wherein the processing circuitry is configured to detect a signal deflection in the cardiac sense signal potentially indicative of an atrial event based on a comparison of the cardiac sense signal to a sense threshold.

4. The implantable medical device according to claim 1, wherein the candidate peak value of a sub-window corresponds to the maximum of the cardiac sense signal in the sub-window.

5. The implantable medical device according to claim 1, wherein the processing circuitry is configured to set the peak amplitude to the maximum of the candidate peak values of the one or more sub-windows.

6. The implantable medical device according to claim 1, wherein the processing circuitry is configured to start, at the end of one sub-window, another sub-window.

7. The implantable medical device according to claim 1, wherein the processing circuitry is configured to detect a signal deflection in the cardiac sense signal potentially indicative of an atrial event within an atrial detection window.

8. The implantable medical device according to claim 7, wherein the processing circuitry is configured to start the atrial detection window based on a comparison of the cardiac sense signal with a start threshold.

9. The implantable medical device according to claim 7, wherein the processing circuitry is configured to start, at the end of each sub-window, another sub-window until the end of the atrial detection window is reached.

10. The implantable medical device according to claim 1, wherein the processing circuitry is configured to detect a signal deflection indicative of a ventricular event caused by ventricular activity succeeding said atrial event, and to define an exclusion interval based on the ventricular event.

11. The implantable medical device according to claim 10, wherein the processing circuitry is configured to exclude a candidate peak value obtained in a sub-window which at least partially overlaps with said exclusion interval.

12. The implantable medical device according to claim 10, wherein the exclusion interval has a first duration, and each sub-window has a second duration corresponding to 1/Z times the first length, Z being a natural number equal to or larger than 1.

13. The implantable medical device according to claim 1, wherein at least some of the sub-windows have a length between 3 ms and 100 ms, for example between 12 ms and 35 ms.

14. The implantable medical device according to claim 1, wherein the processing circuitry comprises a first processing channel having a first gain for processing a first processing signal derived from cardiac sense signals received via the sensor arrangement and a second processing channel having a second gain for processing a second processing signal derived from cardiac sense signals received via the sensor arrangement, the second gain being higher than the first gain.

15. Method for operating an implantable medical device for providing for an intracardiac function, comprising:

receiving, using a sensor arrangement arranged on a body of the implantable medical device, cardiac sense signals; and processing, using a processing circuitry operatively connected to the sensor arrangement, cardiac sense signals received using the sensor arrangement to detect a signal deflection in the cardiac sense signal potentially indicative of an atrial event caused by atrial activity; and to start a peak detection window based on a detection of said signal deflection for determining a peak amplitude associated with said atrial event, wherein the peak detection window comprises one or more sub-windows, the processing circuitry being configured to determine a candidate peak value in each sub-window and to set the peak amplitude based on the valid candidate peak values of one or more consecutive sub-windows, wherein the valid candidate peak values are candidate peak values in valid sub-windows, and wherein a sub-window is considered valid, if this sub-window is not discarded due to being close to a T or QRS wave and/or not discarded due to suspicion of contamination from near-field ventricular activity.

* * * * *